Figure 1:
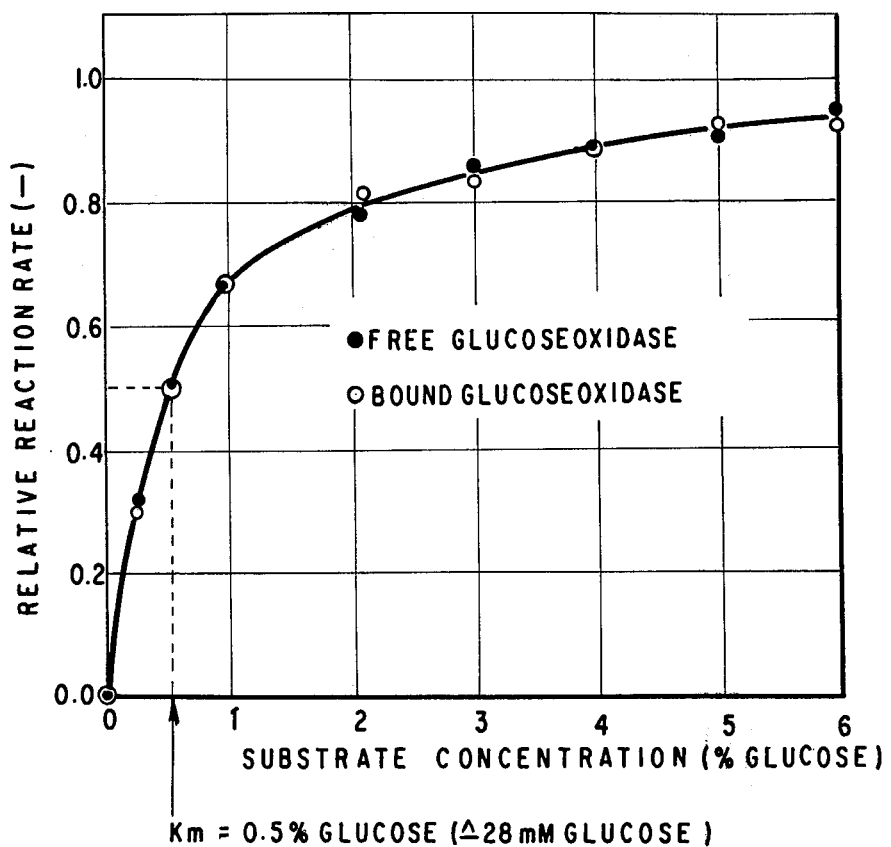

United States Patent [19]

Hartmeier

[11] 4,182,655
[45] Jan. 8, 1980

[54] ENZYME IMMOBILIZATION WITH A PROTEIN CARRIER

[75] Inventor: Winfried Hartmeier, Bingen, Fed. Rep. of Germany

[73] Assignee: Boehringer Ingelheim GmbH, Ingelheim am Rhein, Fed. Rep. of Germany

[21] Appl. No.: 823,007

[22] Filed: Aug. 8, 1977

[30] Foreign Application Priority Data

Aug. 12, 1976 [DE] Fed. Rep. of Germany ....... 2636206

[51] Int. Cl.² .......................... C07G 7/00; C07G 7/02
[52] U.S. Cl. ................................. 435/181; 260/112 R; 260/117
[58] Field of Search .................. 195/63, 68, DIG. 11; 260/112 R, 117

[56] References Cited

U.S. PATENT DOCUMENTS

| 3,705,084 | 12/1972 | Reynolds | 195/63 |
| 3,758,396 | 9/1973 | Vieth et al. | 195/63 X |
| 3,796,634 | 3/1974 | Haynes et al. | 195/63 |
| 3,838,007 | 9/1974 | Van Velzen | 195/63 X |
| 3,841,971 | 10/1974 | Messing | 195/63 |

OTHER PUBLICATIONS

Griffith et al., A New Method for Coating Fermentation Tower Packing so as to Facilitate Microorganism Attachment, Developments in Industrial Microbiology, vol. 17, 4/76, (pp. 241–246).

*Primary Examiner*—David M. Naff
*Attorney, Agent, or Firm*—Hammond & Littell

[57] ABSTRACT

Enzymes are immobilized by mixing an enzyme solution with a dry insoluble crosslinked protein having a water-absorption capacity of 2 to 8 times its dry weight, allowing the protein to swell and suck up the total amount of enzyme solution and mixing the enzyme-containing swollen protein with a solution of glutardialdehyde to bond the enzymes to the protein. Enzymes immobilized by this method are especially well suited for repeated and continuous use.

8 Claims, 1 Drawing Figure

ENZYME IMMOBILIZATION WITH A PROTEIN CARRIER

This invention relates to immobilized enzymes linked by means of glutardialdehyde in the presence of an enzyme-precipitating substance to a water-insoluble, of high-molecular-porous hardened protein, which possesses a 2- to 8-fold capacity of absorbing water based on its dry weight. Furthermore, this invention relates to the production of these immobilized enzymes, as well as to their use for the performance of biotechnical reactions.

BACKGROUND OF THE INVENTION

In the last few years, there became known from the technical and patent literature numerous processes for attachment of enzymes to water-insoluble carriers. A summarizing survey has been made, for example, by R. A. Messing (editor): Immobilized Enzymes for Industrial Reactors, Academic Press, New York, 1975. According to the present state of knowledge, there may be considered 4 ways of attaching an enzyme for making it insoluble: (1) adsorption, (2) ionic binding, (3) encapsulation, and (4) covalent binding to a carrier or cross-linking of the enzymes. Combinations of these basic types of immobilization are also known.

Enzymes linked by adsorption to an enzyme-free carrier, such as activated charcoal or polysaccharides, have the disadvantage that, because of the relatively weak adsorptive attachment, desorption readily occurs. Especially, if changes in the concentration of ions and of temperature occur, a detachment of the adsorption bond may easily take place, and thus the so-called "bleeding-out" of the enzymes.

In case of an ionic binding of the enzyme to a polyanionic or polycationic carrier (as for example ion exchange resins), there exists as well the disadvantage of a relatively weak binding between the polyionic carrier and the enzyme, because the enzyme contains only weakly ionic groups, as a rule. The ion exchange effect of the enzymes thus attached, which leads to the unintended removal of certain ions from a beverage in the course of a treatment of beverages, for example, is a decisive disadvantage which interferes with many reactions.

Enzymes which are encapsulated into polymeric substances (e.g. cross-linked polyacrylamide), have as their main disadvantage the relatively difficult diffusion through the molecular sieve of the inclusion material. The apparent Michaelis constant of an enzyme thus encapsulated is increased thereby, compared even to lower-molecular substrates. In addition, there is the danger that the encapsulated enzymes, due to their elasticity penetrate through the pores of the inclusion material and thus "bleed out."

In the fourth type of attachment mentioned above, the enzyme is covalently and therefore very firmly linked to a reactive group of a water-insoluble carrier. By far the majority of the publications relating to the fixation of enzymes, and the present patent application as well, are concerned with this type of immobilization. A whole range of known immobilized enzyme compositions thus produced are not useful from an economic-technical point of view, however, because they require the use of unduly expensive coupling reagents or carrier substances or excessively costly production processes. In the coupling processes presently know, for instance, a considerable excess of enzymes must be employed, since the major portion of the enzymes is inactivated during the coupling procedure. Most of the processes allow only for a small ratio of enzymes per carrier substance, because the carrier substances can only be covered with enzyme protein on their surface. Partial remedy can be obtained by pulverization (micronization) of the finished products, but these preparations, due to their fineness, can only be passed with difficulties by a stream of liquid, when used in a packed-bed reactor. A further disadvantage of most of the processes for immobilization of enzymes is that the carrier substances, such as glass or diatomaceous earth, are restricted to certain shapes and that it is impossible to give them a ball, splinter or membrane shape or use them as a cover for other materials, such as screens. Some of the carrier substances and coupling reagents are also of doubtful value because of their toxicity.

Several of the above-mentioned disadvantages of known fixed enzymes have been overcome for non-proteolytic enzymes, according to prior art, by coupling these enzymes, for example with glutardialdehyde, to collagen. The preparations thus produced, however, are easily attacked by microbes, and their specific activity is low. A similar situation exists with preparations obtained by cross-linking enzymes with a gel-forming protein (cf. German Offenlegungsschrift No. 2,246,002).

Here, a homogeneous mixture is formed, because enzymes and the gel-forming protein are crosslinked by random. These preparations are more stable towards microbes, but their efficacy is poor, because the enzymes are homogeneously distributed over the whole cross-section of the particle. With respect to high activity, cross-linking can only occur relatively weakly. This leads to such soft preparations that, when used in a packed bed, blocking and bleeding out of the enzymes take place. On the other hand, in case of a stronger cross-linking, this leads to inactivation due to excessively strong bonding and due to the inclusion of internal enzyme molecules. A considerable disadvantage of the last-mentioned fixing processes is also the fact that they cannot be used for proteolytic enzymes.

OBJECTS OF THE INVENTION

It is the object of the present invention to produce water-insoluble non-proteolytic and proteolytic enzymes, which, if possible simultaneously, have the following advantages:
- Cheap method of production,
- Maintainance of a high degree of activity during the fixing procedure as well as after long and repeated use,
- High resistance towards microorganisms,
- Wide variability of the shape of carrier material,
- Good properties when using the packed-bed form,
- High specific activity,
- Low apparent Michaelis constant,
- No undesired ion exchanger or adsorption properties,
- Compatible, non-toxic carriers.

THE INVENTION

I have discovered that immobilized enzymes are obtained which fulfill the above-mentioned criteria, if the enzymes in aqueous dissolved form are first allowed to be soaked up by a swellable, hardened (denatured) protein with a capacity of absorbing water of 2 to 8 times its dry weight, and are subsequently bonded by means of glutardialdehyde in the presence of an enzyme-precipitating substance. Compositions are formed thereby wherein the enzyme is sort of "hung" in certain places onto the exterior and within the high-molecular-porous carrier protein.

Suitable raw materials for the production of the water-insoluble carrier are water-soluble proteins of various types, such as gelatin, egg-white, albumin, soybean protein and the like. It is essential that these proteins can be made water-insoluble by hardening, for example by means of formaldehyde, glutardialdehyde or diisocyanate, and optionally modified by means of other treatment, for example by denaturing action of temperature, so that in a temperature range of between 0° and 100° C. they essentially maintain the capacity to absorb water in an amount equal to 2 to 8 times their dry weight. The swelling behavior of the untreated starting proteins, however, may vary; dry gelatin, for instance, in cold water absorbs only about 10% water (=one tenth of its dry weight), while albumin and egg-white are completely soluble in cold water. However, it is possible to produce from the proteins mentioned above by way of example, as well as from other originally very different proteins, a polymer with the properties desired for the invention in simple manner, namely, by dissolving the starting protein in water at a suitable temperature, cross-linking the same with a hardening or cross-linking agent, such as formalin, and subjecting it then to a drying heat-treatment. In this way the invention does not have to rely on relatively expensive, gel-forming proteins; instead low-grade proteins may be used as well, for example, gelatin with a low Bloom-number or liquid waste gelatin which no longer gels at all, as well as other non-gelling proteins. The production process for the plastic substrate on which the enzymes are going to be fixed may vary within wide limits, depending upon the starting protein which is used, the hardening agent which is used, the available apparatus, the desired shape of the carrier (for instance, chips, balls, membranes, screens or the like), etc. The examples below illustrate several basic possibilities, the desired variations of which are within the judgment and technical abilities of one skilled in the art.

Suitable hardeners are the conventional protein hardening agents, such as formaldehyde, glutardialdehyde or diisocyanate. Especially favorable is the use of formaldehyde, because more enzyme activity can subsequently be bonded to a carrier substance hardened in this way than to a protein hardened, for example, by means of glutardialdehyde. Besides, a carrier cross-linked with glutardialdehyde has an additional, often undesired, tannin-adsorbing property which formaldehyde-hardened proteins do not have. For economic reasons as well, the hardening of proteins with formaldehyde represents a preferred embodiment of the invention.

According to an especially preferred embodiment of the present invention, the water-soluble starting protein envisaged for production of the carrier substance is first introduced into 3 to 10 times its amount of water, based on the weight of dry protein, and the mixture is heated to 40°–80° C. To this protein solution a formaldehyde solution (e.g. formalin) is added in an amount such that about 2 to 5% of formaldehyde, based on the amount of dry protein substance, is admixed with the solution. After some time the stirred solution solidifies, where the solidification period may be shortened in general by applying temperatures as high as possible, a pH-value as close to 8 to 10 as practicable and a high formaldehyde addition. However, normally, a too rapid solidification is not desired, because this would make a homogenous mixing of the protein-formaldehyde-water mixture difficult. Besides, a delayed solidification offers a possibility to bring the carrier into the desired share prior thereto. For example, the carrier may, by the immersion of objects therein (stirrers, screens), be deposited on these objects as a coating, or it may be shaped into very fine spherical particles by means of spray-drying.

Not suitable as carriers for the purpose of the invention are the hardened proteins known as "artificial horn," because it has been found that artificial horn has the capacity to absorb water up to only one-third of its dry weight, that it can be coupled with enzymes only in a very restricted way and that the immobilized enzyme preparations thus obtained reach only a very low specific activity.

For coupling the enzymes with the carrier substrate, it is preferred to use the hardened carriers in the dry condition with the enzymes dissolved in water in an amount such that the total enzyme-containing liquid is sucked up while the water-insoluble carriers are swelling, whereby the exterior and interior surfaces of the carriers are wetted with the enzyme solution. A conventional liquid with enzyme-precipitating activity in which glutardialdehyde is soluble, such as acetone, ethanol or isopropanol, together with glutardialdehyde dissolved in it is added as a coupling reagent. After the enzymes have been bonded, the preparation is washed well with water and either dried in a suitable manner, for example with solvents or by spray drying, or stored in moist condition, if desired under addition of stablizing substances such as glycerin, sorbitol or propyleneglycol, or used directly for its intended purpose.

For the coupling procedure of the enzymes the following conditions are preferably maintained: The aqueous enzyme solution is added in an amount up to 8 times the carrier dry-weight. The liquid with enzyme-precipitating activity is added in an amount such that on the whole, no enzymes the fixing of which is desired will return into solution. Depending upon the enzyme and the precipitating agent these amounts are known to vary greatly, but they may be determined in a simple way by trying them out for each enzyme. Preferably, glutardialdehyde is used in an amount such that its concentration in the reaction batch is between 0.5 and 5%. The whole coupling reaction is preferably effected at room temperature within a period of from 5 minutes to 5 hours.

In contrast to known processes, the process of the present invention can be used to immobilize proteolytically active enzymes as well. It is by means of the hardening of the carriers that it is possible to make the proteins as resistant against proteolytic degradation by the protease to be bound so that the immobilization can be effected without destroying the carrier material. For this purpose pre-hardened proteins capable of absorbing two to four times the amount of water are preferably used as carriers. Carriers that can absorb 4 to 8 times their amount of water are also suitable for certain proteolytic enzymes, such as, for example, Lab. The determination of the appropriate limits in the individual case rest with the expert. If desired, the carrier may be protected from the proteolytic attack of the proteases by applying, for example, lower temperature up to the addition of the substances with enzyme-precipitating activity. After the glutardialdehyde-coupling reaction there is no longer any danger of a degradation of the carrier.

The immobilized enzymes according to the invention are generally suitable for performing the same biotechnical reactions, for which the corresponding soluble enzymes are suited. Moreover, they are especially well suited for repeated and continuous use, as well as for cases where the removal of the enzymes from the reaction mixture, for example from beverages, is desired or prescribed by law. For repeated and long-time use, the high resistance of the preparations against microorganisms, as well as their capability of easy sterilization with known sterilizers, for example, quaternary ammonium compounds, solvents and the like, are particularly favorable.

The following examples illustrate the present invention and will enable others skilled in the art to understand it more completely. It should be understood, however, that the invention is not limited solely to the particular examples given below.

EXAMPLE 1

1 kg of pulverized gelatin (solubilized with alkali, 80 Bloom) was introduced into 6 liters of cold water, and the mixture was heated to 60° C., whereupon the gelatin dissolved. Then, while stirring, 150 ml of formalin (=35% by weight of formaldehyde solution) were added. After 2 minutes and 30 seconds the mass solidified to form a gel. This gelled mass was passed through a meat grinder so that coarse, moist gel-crumbs were formed. In a layer of 5 cm height, the gel-crumbs were dried on a tray in a drying cabinet with air circulation at 115° C. for 15 hours. The dry particles were milled in a blowing mill with screen, so that a particle size distribution between 50 and 100 $\mu$m was obtained. The chip-shaped particles were insoluble in water and had a capacity of absorbing 4.8 times the amount of water, based on their dry weight.

1.5 liters of a solution made up of 0.1 liters of commercial, liquid glucose-oxidase-catalase mixture and 1.4 liters of distilled water were stirred into 0.5 kg of the carrier powder thus obtained. The commercial glucose-oxidase-catalase mixture had a glucose-oxidase activity of 1780 Sarrett-units [SU]/ml and a catalase activity of 880 Baker-units [BU]/ml. Then, 2 liters of acetone and 200 ml of a 25% glutardialdehyde solution were added to the mixture. Afterwards, the reaction mixture was allowed to stand for 60 minutes at 30° C. Then, it was filtered and the solid particles were washed thoroughly on the filter with about 50 liters of distilled water. The residual moist filter cake weighed 1.95 kg. Under addition of 1.05 kg of glycerin, the mass was finely suspended and kept in the refrigerator for further use.

Before examination of the activity as well as before other tests, the glycerin solution was each time rinsed well with water. Table 1 indicates the most important analytical data of the preparation.

Table 1

| | | |
|---|---|---|
| Enzyme-dry substance content | [g/100 g] | 17.6 |
| Glucose-oxidase activity | [SU/g TS] | 178 |
| Catalase activity | [BU/g TS] | 96 |

In order to test the preparation's resistance against washing out, 10 gm were continuously washed in a column with distilled water. At one-day intervals the activity of the enzyme particles was examined. It was found that no significant decrease in activity occurred over 14 days. The same result was obtained when insected of water beer was used as the washing liquid.

The Michaelis constants of the immobilized enzyme preparation as well as those of the soluble glucose-oxidase were determined with glucose as the substrate. No significant difference was found between the dissolved and the immobilized enzyme form, this is shown by FIG. 1 of the attached drawing which represents the relative reaction rate of the soluble and the immobilized enzyme as a function of the glucose concentration.

EXAMPLE 2

3 g of dried egg-white were dissolved in 10 ml of water at 40° C., and the solution was admixed with 0.3 ml of formalin. This mixture was dried in a vacuum-drying chamber at 100° C. and 10–20 mm hg. The dried plastic was ground into a powder having a particle size distribution of 100 to 200 $\mu$m and screened. It was water-insoluble and had a capacity of absorbing water 4 times its dry weight. 0.1 g of a commercial lactase from *Aspergillus flavus*, having a lactase activity of 520 LU/g, was dissolved in 1.5 ml of distilled water. Into this enzyme solution 0.5 g of the plastic powder described above were stirred. Then, while stirring, 3 ml of acetone and 0.25 ml of 25% glutardialdehyde were added. This mixture was allowed to stand for 60 minutes at 25° C. and was then filtered. The bound enzyme remaining as the filter cake was washed out well with distilled water. It had an activity of 42 LU/gm of dry substance. The total quantity of dry substance of the immobilized enzyme preparation amounted to 0.61 gm.

EXAMPLE 3

1 kg of pulverized gelatin (solubilized with acid, 80 Bloom) was stirred into 5 liters of cold water, and the mixture was heated to 45° C. After dissolution of the gelatin, 100 ml of formalin were added. The solution was kept at 45° C. and spray-dried in a laboratory spray-dryer with a two-component nozzle at an air intake temperature of 210° C. and an air outlet temperature of 100° C. and an air rate of 500 Nm$^3$/h. A water-insoluble, fine powder with a capacity of absorbing water 7 times its dry weight was obtained. 0.50 ml of a catalase-free glucose-oxidase solution with an activity of 750 Sarrett-units/ml were admixed with 1 ml of distilled water. Then, 0.5 gm of the above-described pulverized plastic were added. This mixture was admixed with 2 ml of acetone and 0.2 ml of a 25% glutardialdehyde solution and allowed to stand for 60 minutes at room temperature. The preparation was washed out well with distilked water on a filter, A total of 0.59 gm of an immobilized dry enzyme composition was obtained with a glucose-oxidase activity of 290 Sarrett-units per gm of dry substance.

EXAMPLE 4

20 gm of pulverized gelatin (solubilized with acid, 80 Bloom) were dissolved with 100 ml of distilled water, while stirring at 60° C. 2 ml of formalin were added to the dissolved gelatin. Then, a well degreased blade agitator with a blade surface of 20 cm$^2$ was immersed into the gelatin-formalin mixture and removed from it at once. Excess gelatin-formalin mixture was allowed to drip off, and the agitator was put into a drying chamber at 105° C. for drying and cross-linking of the formalin-gelatin mixture. Then the agitator, now covered with a fine plastic layer, was allowed to cool and was dipped into a solution of 20 g of original calf-rennin (Hausen Company) in 100 ml of water for 1 minute. Then the agitator, wetted with rennin, was allowed to stand in a solution of 70 ml of acetone, 30 ml of water and 10 ml of 25% glutardialdehyde for 60 minutes and was subsequently washed for 60 minutes under running water.

In order to examine its milk clotting activity the stirrer was used for stirring slowly 200 ml of fresh whole milk. After about 60 seconds a strong casein precipitation occurred, which proved that the agitator still possessed milk-clotting activity. Then the agitator was rinsed and used again for stirring 200 ml of fresh whole milk. When this procedure had been repeated 10 times, it showed that each time after 50 to 70 seconds a strong casein precipitation took place.

EXAMPLE 5

1 kg of pulverized gelatin (solubilized with alkali, 80 Bloom) was introduced into 6 liters of cold water, and the mixture was heated to 60° C., whereupon the gelatin dissolved. Then, 250 ml of 25% glutardialdehyde solution were added while stirring. After about 2 minutes the mass solidified to form a gel, which was passed through a meat grinder and dried in a layer about 5 cm thick on trays in a drying chamber with air circulation at 120° C.

The dry particles were ground into a powder in a blowing mill with screen, so that a particle size of 50 to 100 μm mostly was obtained. The chip-shaped particles were water-insoluble and had a capacity to absorb 3.1 times their dry weight of water.

1.4 liters of a solution made up from 0.1 liters of a commercial, liquid glucose-oxidase-catalase mixture and 1.3 liters of distilled water were stirred into 0.5 kg of the carrier powder. The commercial glucoseoxidase-catalase mixture had a glucoseoxidase activity of 1780 Sarrett-units/ml and a catalase activity of 800 Baker-units/ml. Then, 2 liters of acetone and 200 ml of 25% glutardialdehyde solution were added to the mixture, and the resulting mixture was allowed to stand for 60 minutes at 30° C. Afterwards, it was filtered and the sold particles were thoroughly washed on the filter with about 50 liters of distilled water. The remaining moist filter cake had a weight of 1.80 kg. It was finely suspended in 1.20 kg of glycerin and stored in a refrigerator for further use.

Before examining the activity as well as before other examinations, the glycerin suspension was rinsed well with water. Table 2 indicates the most important analytical data of the preparation.

Table 2

| Enzyme-dry substance content | [gm/100g] | 17.8 |
| Glucoseoxidase activity | [SU/gm TS] | 134 |
| Catalase activity | [BU/gm TS] | 58 |

With respect to stability to washing out and Michaelis constant compared to the glusoce substrate, the same values as in Example 1, within the limits of analytical error, were found.

EXAMPLE 6

10 kg of pulverized gelatin (solubilized with alkali, 80 Bloom) were introduced into 60 liters of water at about 20° C., and the mixture was heated to 50° C. for 30 minutes. Then, 3.5 liters of formalin were added while stirring. After about 2 minutes, the mass solidified to form a gel which was passed through a meat grinder and dried on trays in layers about 5 cm thick in a drying chamber with air circulation for 24 hours at 108° C. The dry particles were ground into a powder in a blowing mill with screen, so that a carrier powder of 50 to 100 μm particle size was obtained. The chip-shaped particles were insoluble in water and had a capacity of absorbing water 3.2 times their dry weight.

To 5 kg of the carrier powder were added at 0° C. 13 liters of a solution cooled to 0° C., made up from 0.5 kg of commercial papain with an activity of 45,000 NF-units per mgm. Then, 30 liters of isopropanol and 1 liter of 25% glutardialdehyde were stirred in. This reaction mixture was heated to 25° C. within 5 minutes and kept at this temperature for 60 minutes. Afterwards, it was filtered and washed thorougly with about 200 liters of deionized water. The residual filter cake weighing about 18 kg was re-suspended in 20 liters of deionized water, and the suspension was dried in a laboratory spray-dryer with a two-component nozzle at an air intake temperature of 180° C., an air outlet temperature of 85° C. and an air flow rate of 450 Nm$^3$/h. 5.34 kg of a dry immobilized enzyme preparation with an activity of 520 NF-units per mgm were obtained.

EXAMPLE 7

1 kg of commercial amyloglucosidase from *Aspergillus niger* with an activity of 1070 glucoamylase-units per gm was dissolved with 14 liters of deionized water. Then, 5 kg of the carrier powder prepared as described in Example 1 were stirred into the solution. After absorption of the enzyme solution by the carrier powder, 20 liters of acetone and 1 liter of glutardialdehyde were added while stirring, and the mixture was allowed to stand for 60 minutes at 30° C. Afterwards, it was filtered and washed with about 300 liters of water. The residual filter cake was re-suspended in about 30 liters of deionized water and the suspension was dried in a laboratory spray-dryer with a two-component nozzle at 170° C. air intake temperature, 85° C. air outlet temperature and 400 Nm$^3$/h air flow rate. 5.20 kg of a dry immobilized enzyme preparation with an activity of 162 glucoseamylase-units per gm were obtained.

5 liters of hopped, light beer wort were admixed with 20 ml of thick, pasty beer yeast (strain Rh of the of the "Versuchs- und Lehranstalt für Brauerei" in Berlin) and 1 gm of the above-described immobilized amyloglucosidase preparation. Parallel to it, a second batch was prepared in the same manner, but without the amyloglucosidase preparation; both batches were allowed to ferment on a water bath at 8° C. for 7 days. Then the beers were drawn off and the attenuation degree of each was determined by density measurement in the conventional way. The bottom-yeast that settled out in each batch, with and without amyloglucosidase preparation, respectively, was reduced to 20 ml each and used to carry out a further beer fermentation. In this manner the yeast was fermented 4 times. In case of the yeast permeated by amyloglucosidase particles it proved to be relatively simple to lead these particles completely into the next fermentation charge, because after washing of the yeast layer they settled on the bottom of the same. Table 3 reflects the attenuation degrees reached in the 4 fermentations with and without the amyloglucosidase preparation.

Table 3

|  | without preparation | with preparation |
|---|---|---|
| Attenuation degree, 1st fermentation | 78.2% | 89.3% |
| Attenuation degree, 2nd fermentatin | 78.5% | 86.5% |
| Attenuation degree, 3rd fermentation | 77.9% | 87.6% |
| Attenuation degree, 4th fermentation | 78.0% | 84.8% |

EXAMPLE 8

25 gm of liquid waste gelatin without gelling capacity having a 70% dry substance content were dissolved in 100 ml of deionized water at 50° C. 3 ml of formalin were added to the dissolved gelatin. Then, the reaction mixture was poured on a glass plate that had been rubbed before with a greasy cloth, and the mixture was spread to form a thin layer. The glass plates with the reaction mixture thereon were dried in a drying chamber with air circulation at 105° C. After drying, the cross-linked carrier could be detached from the glass plate in membrane form.

A carrier substance membrane thus obtained of 0.1 mm thickness and 5×5 cm size in dry condition was dipped for 2 minutes into a solution of 10 ml of commercial, liquid glucoseoxidase-catalase (as in Example 1) in 50 ml of distilled water. Then, the membrane was put at room temperature for 60 minutes into a mixture of 70 ml of acetone, 30 ml of water and 12 ml of 25% glutardialdehyde. Then the membrane was thoroughly washed with water. Afterwards, it was kept under glycerin until further use. The determination of activity on a part of the membrane resulted in a glucoseoxidase activity of 112 SU/gm of dry substance and a catalase activity of 96 BU/gm of dry substance.

EXAMPLE 9

20 gm of pulverized gelatin (solubilized with acid, 80 Bloom) was dissolved in 100 ml of distilled water at 60° C. while stirring, and 2 ml of formalin were added to the dissolved gelatin. Then, a degreased round screen, 5 cm in diameter, 1 mm-mesh and made of 0.1 mm high-grade steel wire was dipped into the reaction solution and taken out immediately. Excess reaction mixture was blown away with air, so that the wires retained only a thin layer of the reaction mixture. The coated screen was dried for 4 hours at 105° C. in a drying chamber with air circulation. Afterwards, the screen, now covered with a fine layer of carrier substance, was dipped into a solution of 10 ml of commercial, liquid glucoseoxidase-catalase in 50 ml of distilled water for 2 minutes. Then, the screen was placed ar room temperature for 60 minutes into a mixture of 70 ml of acetone, 30 ml of water and 15 ml of 25% glutardialdehyde. Afterwards, the screen was washed thoroughly with water.

In order to examine its enzymatic activity, the screen was placed into 100 ml of a 3.5% glucose solution that was aerated vigorously from below through a frit. The pH-value of this solution was kept at the same level by titration. Table 4 shows the consumption of 0.01 N NaOH, as measured.

Table 4

| Time [min.] | Consumption 0.01 N NaOH[ml] |
|---|---|
| 0 | 0.00 |
| 15 | 0.35 |
| 30 | 0.85 |
| 45 | 1.41 |
| 60 | 1.85 |
| 75 | 2.41 |
| 90 | 2.96 |
| 105 | 3.58 |
| 120 | 4.19 |

Enzyme Activity Determinations

The determination of enzyme activity was effected by the following methods. In case of the fixed enzymes the incubation batches were stirred or shaken, even if this is not indicated in the original description.

Catalase activity: according to First Suppl. Food Chem. Codex, 2nd Ed. page 67–68, published by National Academy of Sciences, Washington, D.C., 1974.

Glucoseoxidase activity: according to First Suppl. Food Chem. Codex, 2nd Ed., page 78–79, published by National Academy of Sciences, Washington, D.C., 1974.

Lactase activity: according to First Suppl. Food Chem. Codex, 2nd Ed., page 81–83, published by National Academy of Sciences, Washington, D.C., 1974.

Amyloglucosidase activity: according to H. J. Pieper, Mikrobielle Amylasen bei der Alkoholgewinnung, page 48–49, published by Verlag Ulmer, Stuttgart, Germany.

Papain activity: according to First Suppl. Food Chem. Codex, 2nd Ed., page 86–87, published by National Academy of Sciences, Washington, D.C. 1974.

I claim:

1. The process for the preparation of an immobilized enzyme composition which comprises dissolving a water-soluble protein in water to form a solution, adding a crosslinking agent to the solution to crosslink the protein and form a gel, drying the gel by heating to form a dried insoluble crosslinked protein having a water-absorption capacity of 2 to 8 times its dry weight, mixing the dry insoluble crosslinked protein with an enzyme-containing solution, allowing the insoluble cross-linked protein to swell and completely suck up the total amount of enzyme solution mixed with the dry insoluble crosslinked protein, and mixing the enzyme-containing swollen insoluble crosslinked protein with a solution of glutardialdehyde in a lower aliphatic alcohol or ketone to provide 0.5 to 5% glutardialdehyde in the resultant reaction mixture to bond the enzymes to the swollen insoluble crosslinked protein to provide the immobilized enzyme composition.

2. The process of claim 1, where said crosslinking agent is formaldehyde.

3. The process of claim 1, where said water-soluble protein is gelatin and said crosslinking agent is formaldehyde.

4. The process of claim 1, where the enzyme immobilizing procedure is effected within a period of 5 minutes to 5 hours.

5. An immobilized enzyme composition prepared according to the process of claim 1.

6. The enzyme composition prepared according to the process of claim 2.

7. The enzyme composition prepared according to the process of claim 3.

8. The enzyme composition prepared according to the process of claim 4.

* * * * *

UNITED STATES PATENT AND TRADEMARK OFFICE
CERTIFICATE OF CORRECTION

PATENT NO. : 4,182,655
DATED : January 8, 1980
INVENTOR(S) : WINFRIED HARTMEIER

It is certified that error appears in the above-identified patent and that said Letters Patent are hereby corrected as shown below:

Column 4, line 35: "propyleneg" should read -- propylene -- line 36: "lycol" should read -- glycol --.

Column 6, lines 1 and 2: "inserted" should read
-- instead --.

Signed and Sealed this

Twenty-fifth Day of March 1980

[SEAL]

Attest:

SIDNEY A. DIAMOND

Attesting Officer     Commissioner of Patents and Trademarks